United States Patent
Presura et al.

(10) Patent No.: US 10,617,308 B2
(45) Date of Patent: *Apr. 14, 2020

(54) DEVICE AND METHOD FOR ESTIMATING THE HEART RATE DURING MOTION

(71) Applicant: KONINKLIJKE PHILIPS N.V., Eindhoven (NL)

(72) Inventors: Cristian Nicolae Presura, Veldhoven (NL); David Antoine Christian Marie Roovers, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/678,140

(22) Filed: Aug. 16, 2017

(65) Prior Publication Data
US 2018/0028075 A1 Feb. 1, 2018

Related U.S. Application Data

(63) Continuation of application No. 14/239,699, filed as application No. PCT/IB2012/054553 on Sep. 4, 2012, now Pat. No. 9,770,176.

(Continued)

(51) Int. Cl.
*A61B 5/0205* (2006.01)
*A61B 5/00* (2006.01)
(Continued)

(52) U.S. Cl.
CPC ........ *A61B 5/0205* (2013.01); *A61B 5/02416* (2013.01); *A61B 5/02438* (2013.01);
(Continued)

(58) Field of Classification Search
CPC .............. A61B 5/02416; A61B 5/0205; A61B 5/02438; G06F 19/3431
See application file for complete search history.

(56) References Cited

U.S. PATENT DOCUMENTS

| 4,192,000 A | 3/1980 | Lipsey |
| 4,312,358 A * | 1/1982 | Barney .............. A61B 5/02438 |
| | | 235/91 H |

(Continued)

FOREIGN PATENT DOCUMENTS

| CN | 101730503 A1 | 6/2010 |
| EP | 0733340 A1 | 9/1996 |

(Continued)

OTHER PUBLICATIONS

M. Bodner and E. Rhodes, "A Review of the Concept of the Heart Rate Deflection Point", Sports Medicine, vol. 30, No. 1, pp. 31-46, 2000.*

(Continued)

*Primary Examiner* — Lynsey C Eiseman
*Assistant Examiner* — Amanda L Steinberg

(57) ABSTRACT

The present invention relates to a portable device for determining a heart rate of a person, said portable device comprising:
- a heart rate measurement unit for measuring the heart rate of the person over time to generate a heart rate signal,
- a motion measurement unit for measuring the motion of a body part of the person over time to generate a motion signal, and
- a processing unit which is adapted to measure a signal quality of the heart rate signal, to calculate the heart rate based on the heart rate signal if said signal quality is above a predefined threshold, and to estimate the heart rate based on the motion signal if said signal quality is below said threshold.

14 Claims, 9 Drawing Sheets

Related U.S. Application Data

(60) Provisional application No. 61/535,396, filed on Sep. 16, 2011.

(51) Int. Cl.
*A61B 5/024* (2006.01)
*A61B 5/11* (2006.01)

(52) U.S. Cl.
CPC ............ *A61B 5/1118* (2013.01); *A61B 5/681* (2013.01); *A61B 5/721* (2013.01); *A61B 5/7278* (2013.01)

(56) References Cited

U.S. PATENT DOCUMENTS

| | | | |
|---|---|---|---|
| 5,749,366 A * | 5/1998 | Odagiri | A61B 5/024 600/500 |
| 6,449,501 B1 * | 9/2002 | Reuss | A61B 5/14551 600/322 |
| 2002/0035315 A1 | 3/2002 | Ali et al. | |
| 2002/0068873 A1 | 6/2002 | Nissila | |
| 2003/0065269 A1 | 4/2003 | Vetter et al. | |
| 2004/0122333 A1 | 6/2004 | Nissila | |
| 2004/0186387 A1 | 9/2004 | Kosuda et al. | |
| 2005/0113703 A1 | 5/2005 | Farringdon et al. | |
| 2005/0228301 A1 | 10/2005 | Banet | |
| 2005/0245793 A1 | 11/2005 | Hilton | |
| 2006/0084879 A1 | 4/2006 | Nazarian et al. | |
| 2007/0195989 A1 | 8/2007 | Tsubata et al. | |
| 2008/0214963 A1 | 9/2008 | Guillemaud et al. | |
| 2008/0294058 A1 * | 11/2008 | Shklarski | A61B 5/02055 600/502 |
| 2009/0018405 A1 | 1/2009 | Katsumura et al. | |
| 2009/0082681 A1 | 3/2009 | Yokoyama et al. | |
| 2009/0112111 A1 | 4/2009 | Shimizu et al. | |
| 2010/0160794 A1 | 6/2010 | Banet | |
| 2011/0066051 A1 | 3/2011 | Moon et al. | |
| 2011/0066381 A1 | 3/2011 | Garudadri et al. | |
| 2012/0283525 A1 | 11/2012 | Kuroda | |

FOREIGN PATENT DOCUMENTS

| | | |
|---|---|---|
| EP | 1908401 A1 | 4/2008 |
| JP | 2005323734 A | 11/2005 |
| JP | 2009072417 | 4/2009 |
| JP | 2012232010 | 11/2012 |
| WO | WO2008110788 A1 | 9/2008 |

OTHER PUBLICATIONS

Brage et al "Reliability and Validity of the Combined Heart Rate and Movement Sensor Actiheart", European Journal of Clinical Nutrition (2005) 59, p. 561-570.

Renevey et al, "Wrist-Located Pulse Detection Using IR Signals, Activity and Nonlinear Artifact Cancellation", Proceedings of the 23rd Annual EMBS International Conference, vol. 3, Oct. 25, 2001, pp. 3030-3033.

M. Bodner and E. Rhodes, "A Review of the Concept of the heart Rate Rate Deflection Point", Sports Medicine, vol. 30, No. 12, pp. 31-46, 2000.

PCT International Search Report, International application No. PCT/IB2012/054553, dated Sep. 4, 2012.

* cited by examiner

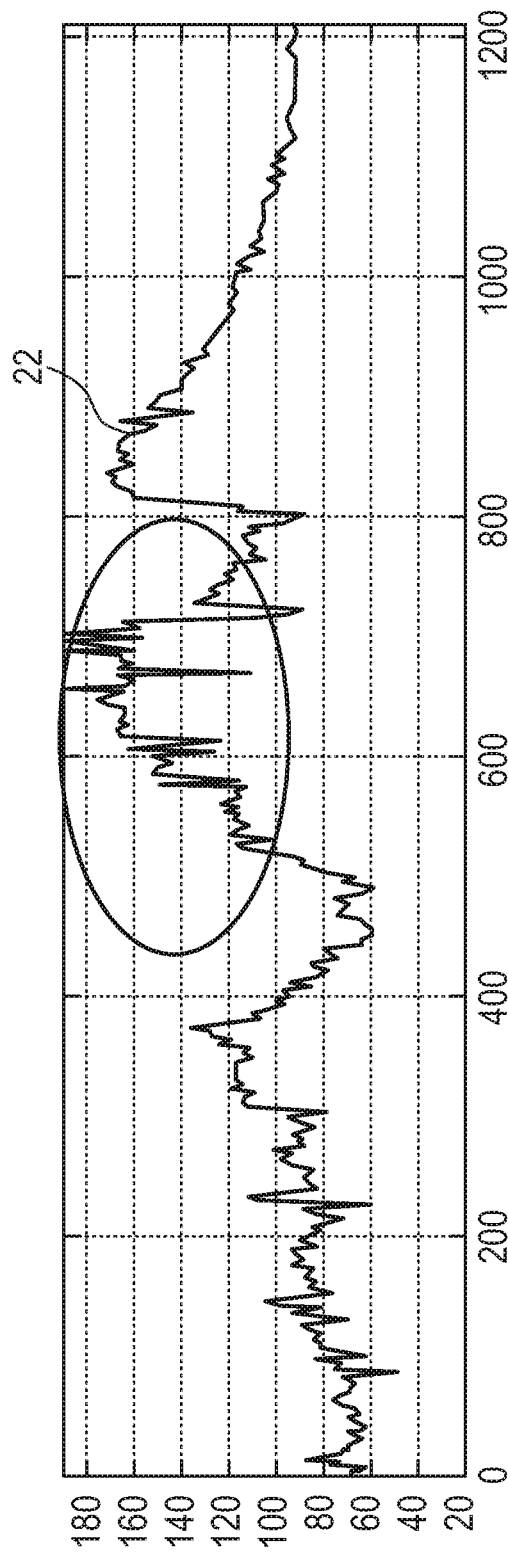
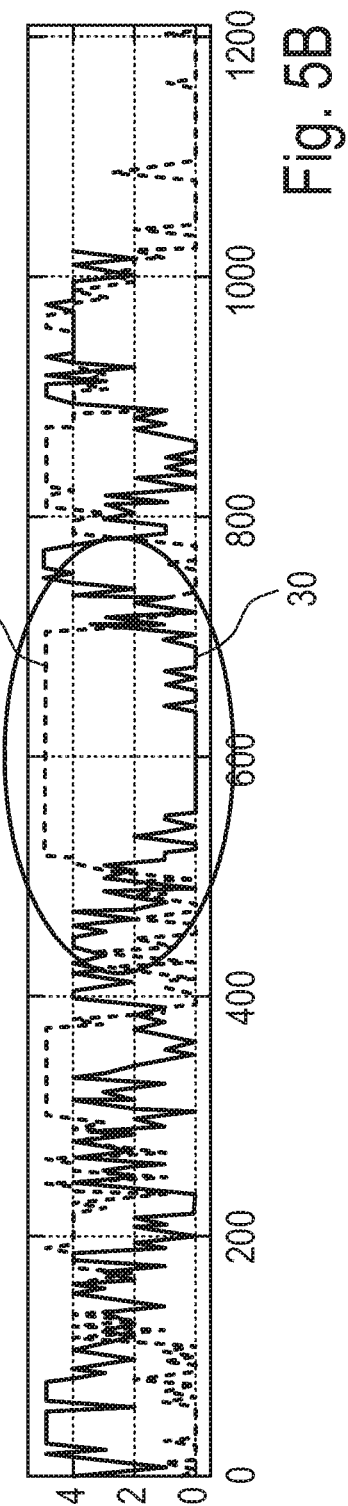

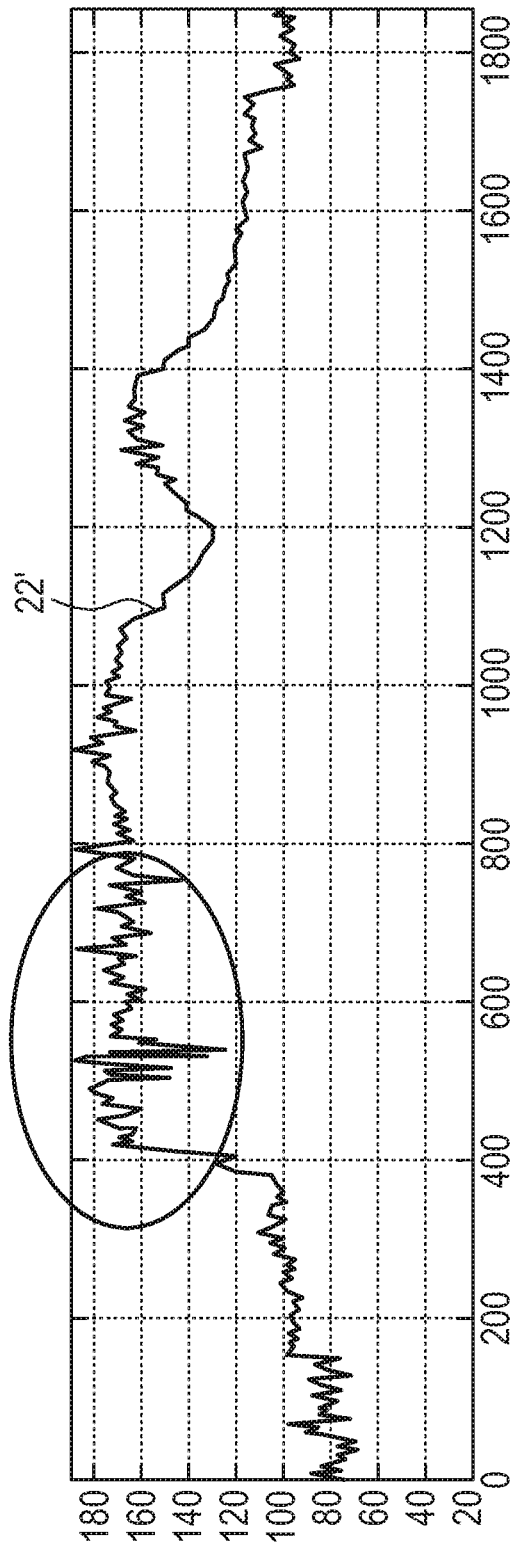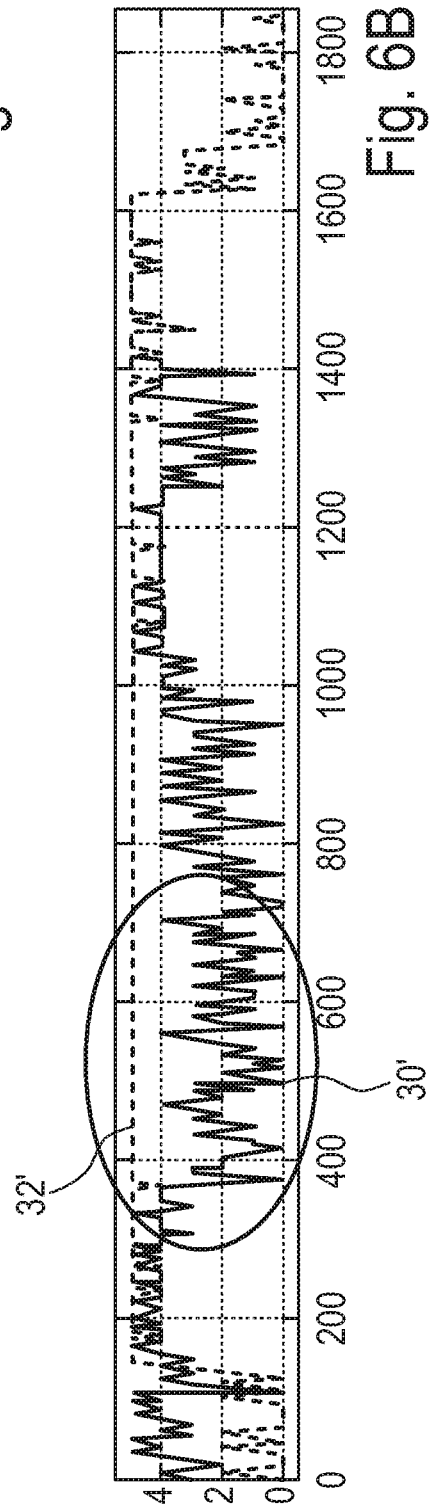

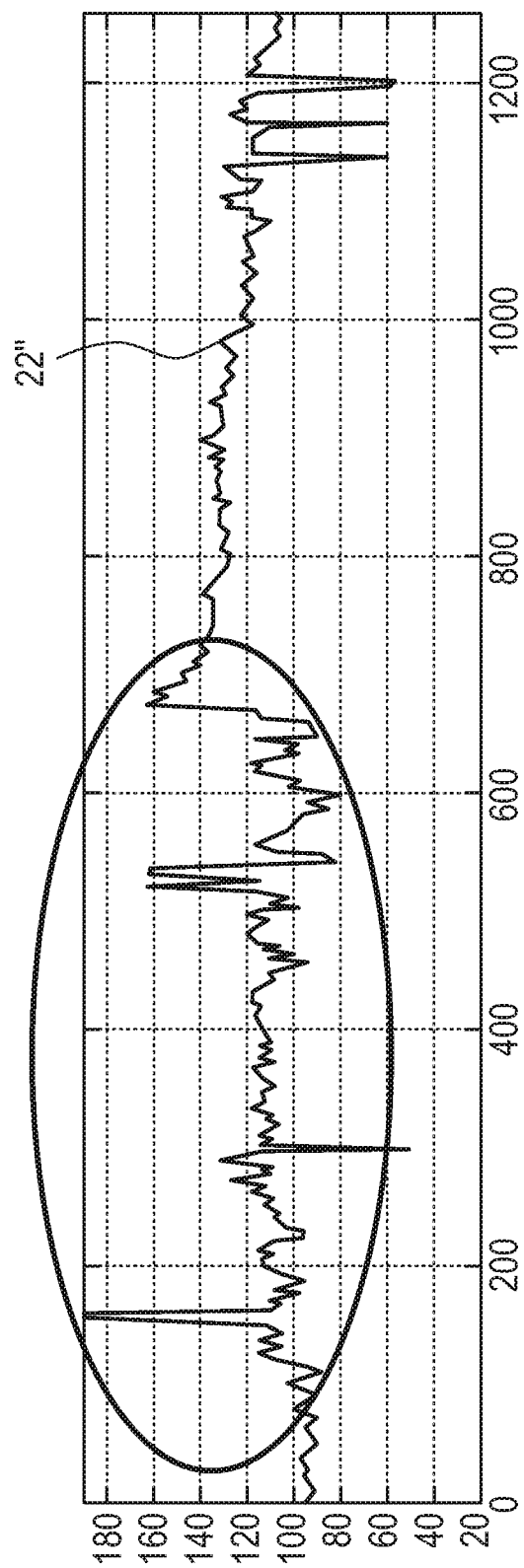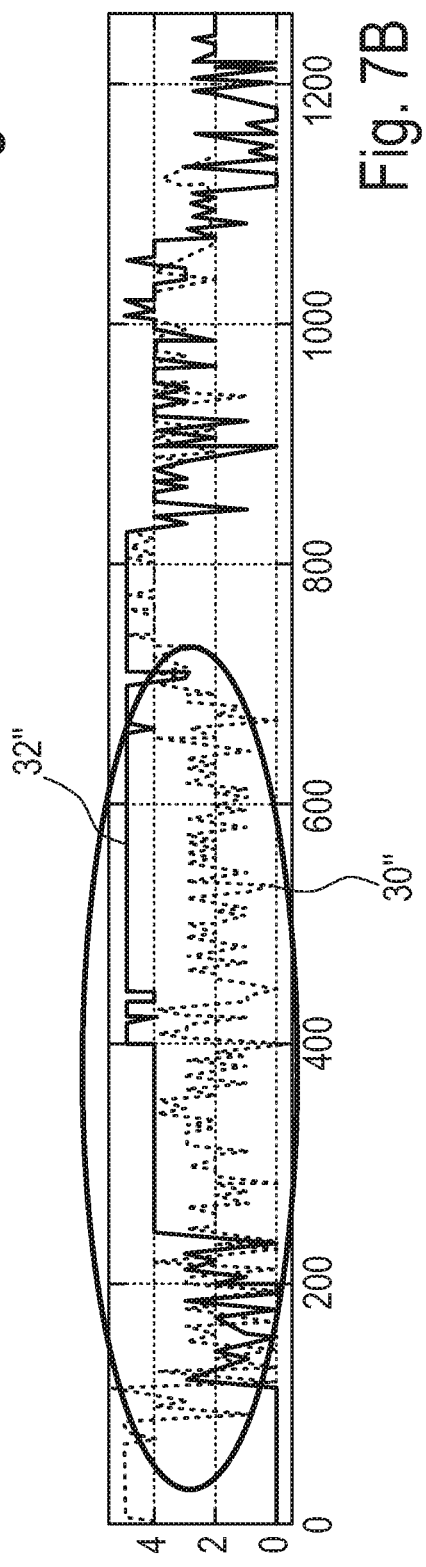

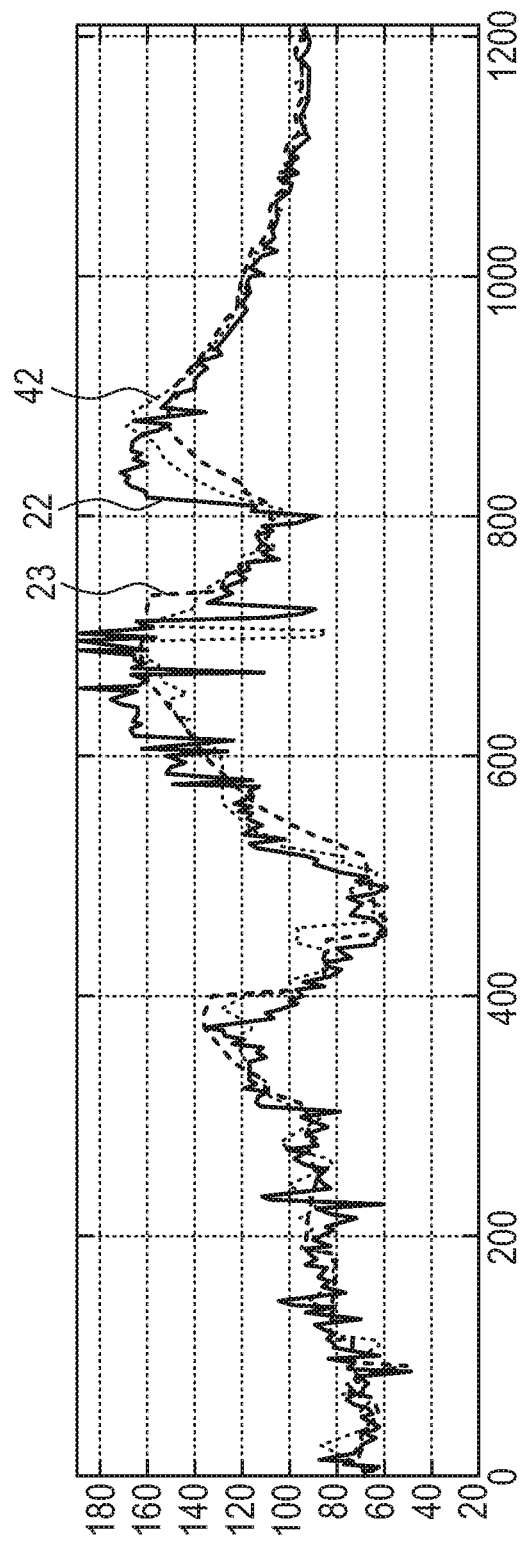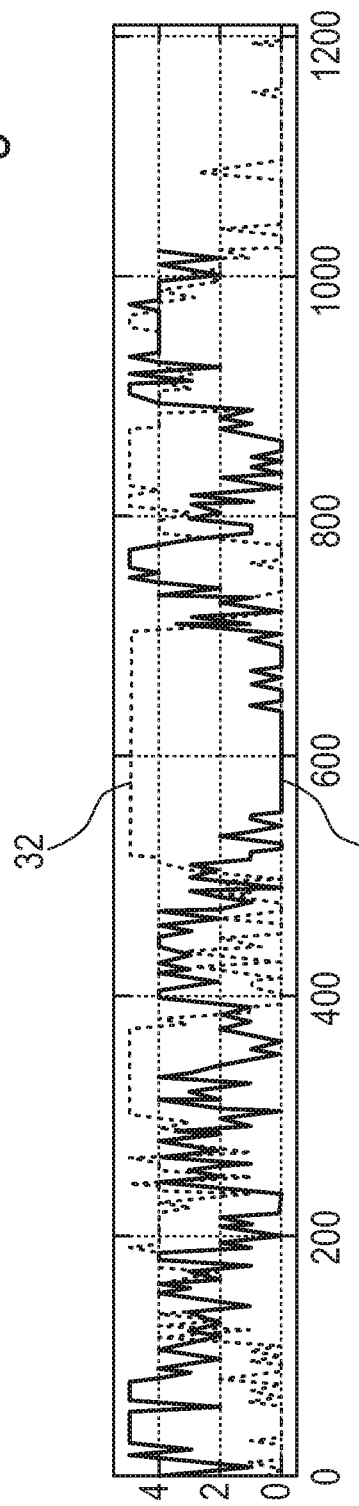

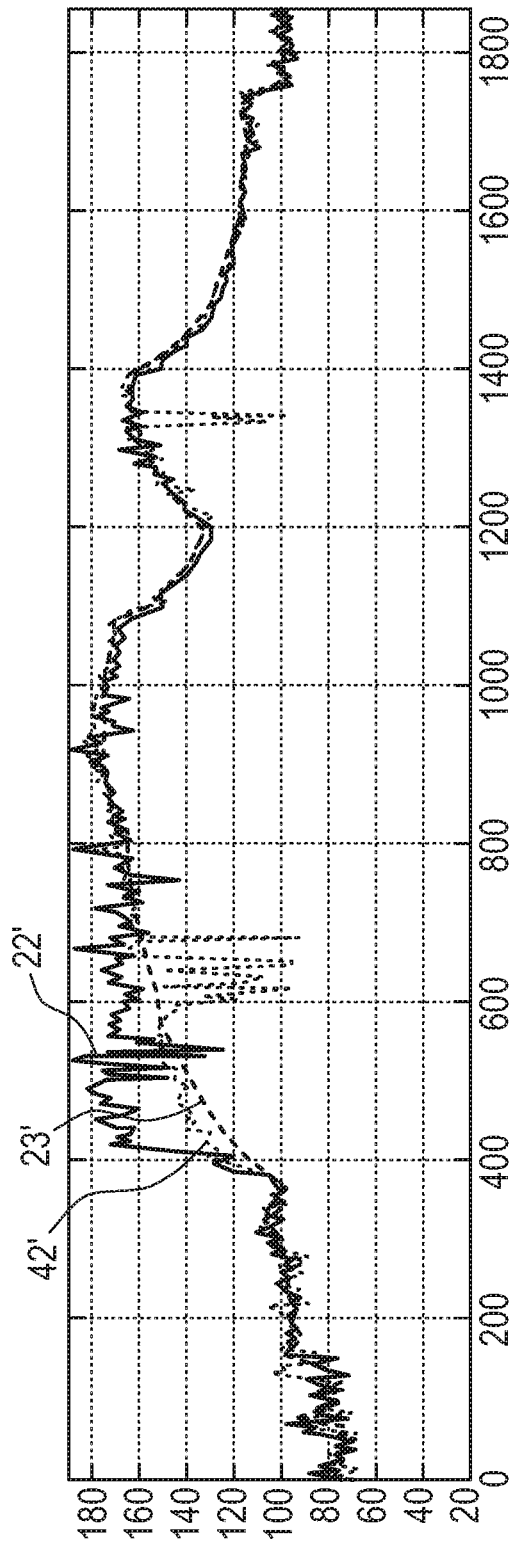
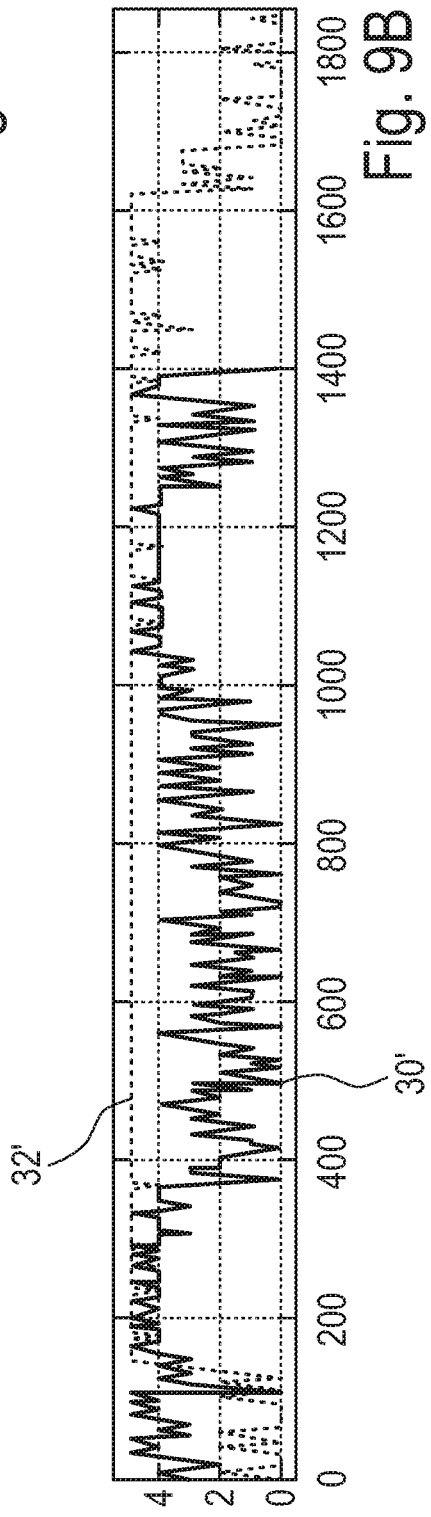

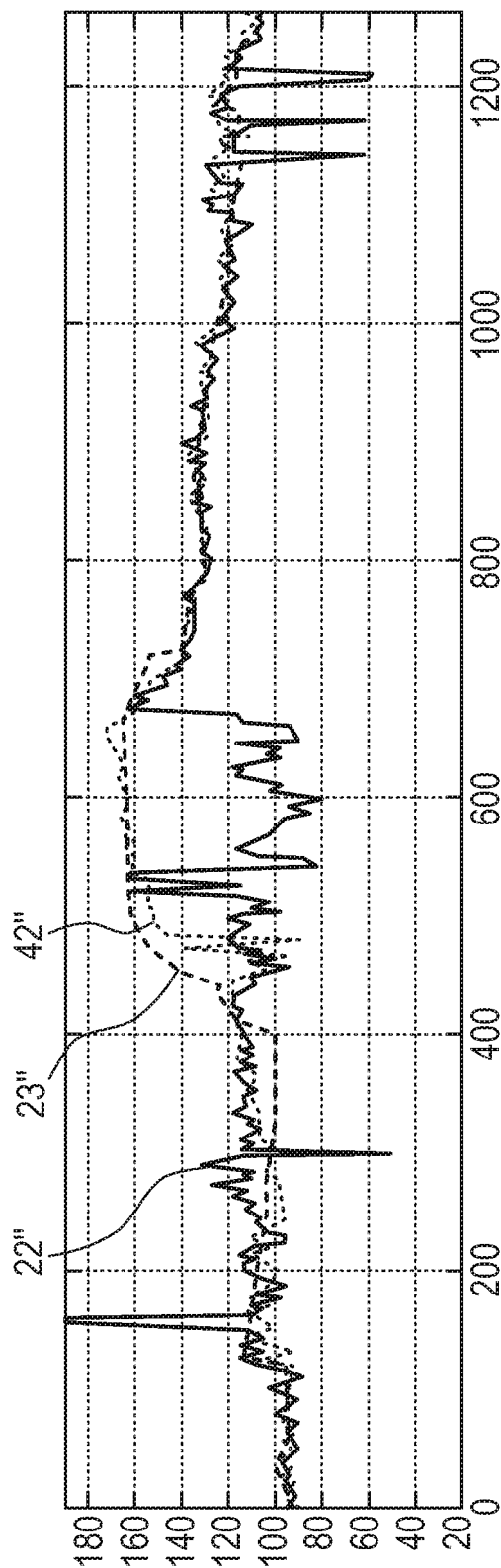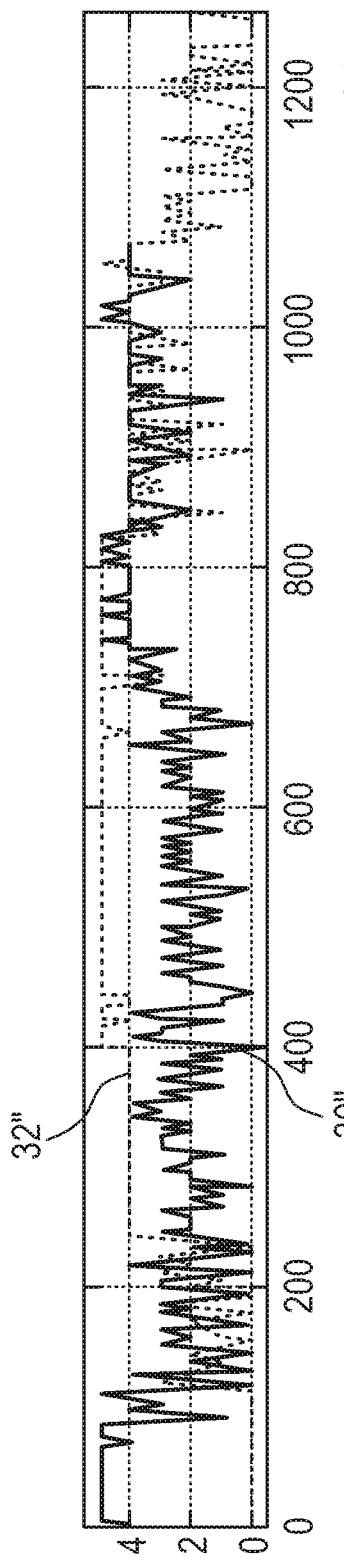

DEVICE AND METHOD FOR ESTIMATING THE HEART RATE DURING MOTION

CROSS-REFERENCE TO RELATED APPLICATIONS

This application is a continuation under 35 U.S.C. § 120 of U.S. patent application Ser. No. 14/239,699, filed Feb. 19, 2014, which claimed priority to PCT Application PCT/IB2012/054553 filed Sep. 4, 2012, which claimed priority to the provisional U.S. Patent Application No. 61/535,396, filed Sep. 16, 2011, the contents of which are incorporated herein by reference.

FIELD OF THE INVENTION

The present invention relates to a portable device for determining the heart rate of a person. The invention further relates to a corresponding method and a system. Even further, the present invention relates to a computer program for controlling said device to carry out the steps of said method.

BACKGROUND OF THE INVENTION

Due to the growing number of people that live an inactive life, many physical activity promotion products and services have been developed over the last decades, both for research and commercial objectives. Said physical activity promotion products in most cases try to calculate or estimate the heart rate in order to display the person's pulse during a physical activity. At present, the most successful devices that measure the heart rate for athletes make use of a chest belt. These devices measure the electric signal of the heart (ECG) during the athlete's physical activity. However, these chest straps are uncomfortable to wear, which practically restricts their use to serious athletes.

Because more and more people are aware of the power of monitoring heart rate for their health, and most people try to avoid wearing such a kind of chest strap due to its uncomfortableness, the paradigm of measuring a heart rate slowly changes from high resolution and low comfort to medium resolution but higher wearing comfort.

This is achieved, for example, through optical heart rate monitors, which may be attached to different parts of the body, e.g. also to the wrist of the athlete. A device of this kind, which is known from the prior art, is commercially distributed under the name ePulse2™. This heart rate monitor includes an optical sensor that is similar to pulse oximeters available in the market. It is realized as an arm band that can be worn conveniently on the wrist.

Optical sensors used for heart rate measurement, however, suffer from large movement artifacts, especially in case of large and fast movements as these occur during a physical activity like running, cycling or rowing. That is because the optical sensor in fact optically measures the blood flow inside the blood vessel, which blood flow is, of course, also influenced by the body movement, so that discontinuous, rough movements occur within the blood vessel. This results in large movement artifacts, which complicate the heart rate measurement.

For this reason, some optical sensors known from the prior art use an additional motion sensor to measure the occurring motion of the body part and to compensate for the resulting motion artifacts. However, there is a limit. When the movement of the body part, to which the sensor is attached, becomes very large, the optical sensor does not provide reliable measurements anymore, even when the measurement signal is compensated, respectively adapted with the motion signal provided from the motion sensor.

In this case, the heart rate monitor either displays a wrong heart rate value or no heart rate value at all. This is regarded to be a major disadvantage, since the measurement results in an inaccurate or no displayed heart rate.

Several years of experience with a large set of users have shown that participants attach high importance to the reliability and the comfort of such heart rate measurements. In particular, when athletes or sportsmen have engaged in heavy activity or exercise they consider it necessary to have a reliable, real time feedback of the current heart rate at all times. If the heart rate monitor has registered a wrong heart rate or does not even display a value of the heart rate, this can be experienced as de-motivating and has a negative impact on the overall perception of the device.

SUMMARY OF THE INVENTION

It is an object of the present invention to provide a device, a method, a system and a corresponding software of the kind mentioned initially, which enable an improved heart rate measurement, wherein the heart rate is measured in a comfortable way for the user and the measurement still delivers reliable measurement results even when strong motions occur at the measured body part of the user. It is in particular an object of the present invention, to calculate or estimate the heart rate to the largest degree of accuracy and to overcome the problem of large movement artifacts within the heart rate signal that may lead to a failure of the heart rate measurement.

In a first aspect, this object is according to the present invention achieved by a portable device for determining a heart rate of a person, said portable device comprising:
  a heart rate measurement unit for measuring the heart rate of the person over time to generate a heart rate signal,
  a motion measurement unit for measuring the motion of a body part of the person over time to generate a motion signal, and
  a processing unit which is adapted to measure a signal quality of the heart rate signal, to calculate the heart rate based on the heart rate signal if said signal quality is above a predefined threshold, and to estimate the heart rate based on the motion signal if said signal quality is below said threshold.

In a second aspect of the present invention, a corresponding method is presented, which includes the steps of:
  measuring the heart rate of the person over time to generate a heart rate signal,
  measuring the motion of a body part of the person over time to generate a motion signal,
  measuring a signal quality of the heart rate signal, and
  calculating the heart rate based on the heart rate signal if said signal quality is above a predefined threshold, and estimating the heart rate based on the motion signal if said signal quality is below said threshold.

In a third aspect of the present invention, a system for determining a heart rate of a person is presented, said system comprising:
  a portable heart rate measurement device for measuring the heart rate of the person over time to generate a heart rate signal,
  a portable motion measurement device for measuring the motion of a body part of the person over time to generate a motion signal, and a processing device which comprises a communication interface for receiving said heart rate signal and said motion signal, and a processing means which is adapted to measure a signal quality of the heart rate signal, to calculate the heart rate based on the heart rate signal if said signal quality is above a predefined threshold, and to estimate the heart rate based on the motion signal if said signal quality is below said threshold.

In a still further aspect of the present invention, a computer program product is presented comprising program code means for causing a computer to control said portable device to carry out the steps of said method when said computer program is carried out on the computer.

Preferred embodiments of the invention are defined in the dependent claims. It shall be understood that the claimed method and the claimed system have similar and/or identical preferred embodiments as the claimed portable device and as defined in the dependent claims.

It has been recognized by the inventors that the heart rate may still be estimated in a reliable manner even when the heart rate signal, which is generated by the heart rate measurement unit, becomes unreliable due to movement artifacts. According to the invention, the heart rate is in such cases estimated based on the motion signal that is provided by the motion measurement unit. Estimating the heart rate based on the motion signal means that the heart rate is estimated based on at least the motion signal, which again means that also other parameters and signals may be included into this estimation. In order to implement this kind of heart rate measurement, the processing unit is adapted to measure the signal quality of the heart rate signal. In case the heart rate signal is above a predefined threshold value, the heart rate may be measured based on the heart rate signal. This may be done by a frequency evaluation of the heart rate signal, which results in a determination of the pulse of the person.

If on the other hand, the signal quality of the heart rate signal is detected to be below said predefined threshold, the heart rate may be estimated based on the motion signal. Thereto, the processing unit is adapted to switch from a first mode, in which the heart rate is calculated from the measured heart rate signal, to a second mode, in which the heart rate is estimated based on the measured motion signal. The switch between these two modes depends on the threshold value.

Said threshold value indicates a level of noise within the heart rate signal, wherein the heart rate signal measured by the heart rate measurement unit becomes unreliable when exceeding a certain level of noise, respectively when underrunning said threshold. In other words, said threshold value indicates a minimum signal quality of the heart rate signal that is needed to reliably calculate the heart rate based on the heart rate signal. The threshold value may be determined from experiments that evaluate at what level of motion of the device the movement artifacts that are induced into the heart rate signal become so large or strong, that a reliable measurement of the heart rate cannot be extracted simply from the heart rate signal anymore. This threshold or threshold level of noise does not necessarily need to be an exact value. It may also be a range of values where the signal quality of the heart rate signal transitions from a good or sufficient measurement quality to a low, insufficient measurement quality. In still other words, the threshold value indicates the lowest possible signal quality level of the heart rate signal, below which a calculation of the heart rate based on the heart rate signal would lead to a failure, respectively to a wrong heart rate value that is outside a tolerable failure range.

By making use of the motion signal, it is possible to reliably estimate the heart rate, also in cases in which the heart rate signal is unusable due to large motion artifacts. This is a major advantage compared to the devices of the prior art mentioned initially, since the user receives a reliable feedback of its heart rate/pulse, even in cases where the device is subjected to high accelerations or strong vibrations.

In contrast to the prior art devices, the presented portable device thus allows to provide a heart rate to the user at all times, even in instances, in which the heart rate measurement unit fails.

Estimating the heart rate based on the motion signal does not necessarily mean that the motion signal, only, is taken into account to estimate the heart rate. Even in the above-mentioned cases, in which the signal quality of the heart rate signal is below the predefined threshold, the heart rate signal may still be taken into account. In such an embodiment the processing unit is adapted to correct, respectively adapt the heart rate signal based on the information taken from the motion signal. In other words, the heart rate signal is in this case corrected with correction values that may be determined from the motion signal, e.g. filtering the noise that occurs within the heart rate signal by comparing/substracting the motion induced signal parts from the heart rate signal.

Even though the heart rate may be directly calculated from the heart rate signal if the signal quality of the heart rate signal is above said predefined threshold, the processing unit may, according to an embodiment of the invention, be adapted to calculate the heart rate based on the heart rate signal and to adapt the calculated heart rate based on the motion signal. However, this is not necessarily needed when the heart rate can be measured in a reliable manner. Nevertheless, this measure can be implemented as a further improvement of the heart rate measurement.

According to the invention, the heart rate measurement unit can be realized by any kind of sensor that enables to measure the heart rate of a person over time. This may also include an electrical ECG electrode. According to a preferred embodiment of the present invention the heart rate measurement unit comprises an optical sensor, in particular a photoplethysmography (PPG) sensor for measuring a blood pulse wave of the person over time to generate the heart rate signal. The PPG sensor includes a photo detector that, in the normal way, measures the absorbance of the blood at different wavelengths allowing a determination of the light absorbance due to the pulsing arterial blood.

Such a kind of PPG sensor enables to measure the pulse of the person in a comfortable way. The portable device may, for example, be attached to the wrist of the person. In contrast to known PPG sensors that are usually attached to the fingertip or the earlobe of the person, an attachment on the wrist of the person allows an appliance of the portable device for different kinds of sport activities, wherein the device may comfortably be worn. Even though an attachment on the wrist is preferred, the portable device may also be attached to any other body part of the person, e.g. the chest, a leg or around the neck.

The above-mentioned motion measurement unit preferably comprises an inertial sensor for measuring an acceleration of the body part to which it is attached in at least one spatial dimension. This inertial sensor is preferably adapted to perform a three-axial accelerometry. Thereto, it is preferably equipped with three accelerometers and/or three gyroscopes. The accelerometers are placed such that their measuring axes are perpendicular to each other, in order to being able to measure the G-forces in all three spatial dimensions. The three gyroscopes are placed in a similar perpendicular pattern, which enables to measure the rotational position of the device in reference to an arbitrarily chosen coordinate system. It is to be understood that the gyroscopes are not necessarily needed, since the accelerometers measuring the acceleration in the different spatial directions are sufficient for the most appliances. Further, it is to be noted that a single accelerometer is also sufficient to generated the desired motion/acceleration signal.

The portable device is preferably designed in a shape that is similar to a watch. According to an embodiment of the present invention, the portable device comprises a display for displaying the calculated heart rate. This display enables to provide the user with the measured heart rate/pulse in real time. This display may be realized in different ways, e.g. as an LED array.

According to an embodiment of the present invention, the processing unit is adapted to determine the signal quality of the heart rate signal in the frequency domain by analyzing the spectral peaks of the heart rate signal at the heart rate frequency and/or its harmonics.

In this analysis the height, respectively the magnitude of these peaks is investigated. This gives an indication of the signal power of the heart rate signal. In general, it can be stated that the higher and the clearer the peaks are developed in the frequency domain, the better is the signal quality of the heart rate signal. This mainly relies on the fact that the blood pulse wave ideally generates a periodic signal, which in the frequency domain results in clear peaks at or near the heart rate frequency and/or its harmonics.

A clear peak at the heart rate frequency and/or its harmonics is thus an indicator for a periodic signal, which again is an indicator for a good signal quality of the heart rate signal. If, on the other hand, the heart rate signal is corrupted by the occurring motion and includes motion artifacts, this will result in different noisy peaks within the power spectrum. Generally speaking, the signal quality can thus be determined based on the spectral peaks of the heart rate signal.

If clear peaks occur at or around the heart rate frequency and/or its harmonics, the signal quality is reliable enough to calculate the heart rate based on the heart rate signal (first mode). If on the other hand, the spectral analysis of the heart rate signal shows a noisy spectrum, the processing unit switches to the second mode, in which the heart rate is estimated based on the motion signal.

In an embodiment, the portable device further comprises a frequency filter to filter out the frequency components within the heart rate signal which are due to motion of the device, wherein the processing unit is adapted to determine the signal quality of the filtered heart rate signal. This filter enables an easier detection of the heart rate from the heart rate signal. However, this is not a necessary feature, since in practice the frequency components which are due to motion occur at different frequencies than the frequency components that are due to the heartbeat. In practice, it is thus in most cases possible to clearly distinguish between the different kinds of frequency components, especially when analyzing the heart rate signal in the frequency domain.

Instead of analyzing the heart rate signal in the frequency domain, the processing unit may also be adapted to determine the signal quality of the heart rate signal in the time domain by analyzing the height of the peaks in the autocorrelation function at the heart rate period and its multiples. In case of analyzing the heart rate signal in the time domain, the processing unit measures the level of signal quality depending on the periodic components within the signal, which again are an indicator for a reliable heart rate signal. This may, for example, be done by counting the zero crossings and/or the signal peaks, or by analyzing the consistency of the signal peaks. Similarly as mentioned above, the processing unit then decides, depending on the signal analysis, if the heart rate is calculated based on the heart rate signal (first mode), or if the heart rate is estimated based on the motion signal (second mode).

The estimation of the heart rate based on the motion signal in the second working mode of the processing unit is preferably done as follows:

According to an embodiment of the present invention, the processing unit is adapted to estimate the heart rate based on the motion signal by estimating a heart rate constant ($HR_{constant}$) and defining an exponential development of the heart rate over time, wherein the exponential development of the heart rate starts at the last reliably measured heart rate and finishes at the estimated $HR_{constant}$. The $HR_{constant}$ is an estimated heart rate of the person which depends on the frequency of the motion signal, and the last reliably measured heart rate is the last measured heart rate with the heart rate measurement unit at a point in time before underrunning said level of signal quality.

The processing unit thus estimates the heart rate in two steps. In a first step, $HR_{constant}$ is estimated. The estimation of the $HR_{constant}$ requires an estimation of the present motion, respectively an estimation of the frequency of the device motion (the frequency of the motion of the measured body part). This frequency can be derived from the measured motion signal.

The $HR_{constant}$ indicates a pulse level of the person to which the person's pulse would increase or decrease if the amount and intensity of motion would be kept constant for a long time. In other words, the estimation is based on the assumption that the person's movement is kept constant during the so-called transition period, in which the device switches to the second mode, in which the heart rate is estimated based on the motion signal. Since the transition period in practice is only a very short time period of several seconds, this assumption has shown to result in a good approximation.

Once the $HR_{constant}$ is determined, the processing unit defines an exponential development of the heart rate over time with a start value at the last reliably measured heart rate that has been measured based on the heart rate signal and a terminal value that equals the $HR_{constant}$. It has been shown that an exponential development reflects the natural behavior of the human heart in a good and precise manner.

This exponential behavior is an approximation curve for a person's pulse in-/decrease. This in-/decrease also depends on the physical fitness of the person. The exponential approximation curve thus preferably has a time constant a, wherein a being a constant related to the person's fitness which decreases with increasing fitness.

According to an embodiment of the present invention the processing unit is adapted to calculate the $HR_{constant}$, with $HR_{constant}=2,1*f-a$, where f is the frequency of the motion signal, and a is the constant indicating the person's fitness with $a=75-HR_{rest}$, and $HR_{rest}$ being the resting heart rate of the person.

It is to be noted, that the above relation between the $HR_{constant}$ and the intensity of the person's physical activity, which is indicated by the motion frequency of the measured body part, is a linear relation. This relation has been found on the basis of experiments that have been performed by the applicant. These experiments have shown that the $HR_{constant}$ stays at a value that is about two times the motion frequency. A good approximation for the fitness parameter a has been found to be $a=75-HR_{rest}$.

The resting heart rate $HR_{rest}$ may, for example, be measured directly using the presented portable device measuring the heart rate, when the user rests, i.e. when the user is not moving. Furthermore, the $HR_{rest}$ may also be estimated from the heart rate signal during the regular heart rate measurement (in the first working mode of the processing unit). However, it is to be noted that also other values can be chosen for a, $HR_{rest}$ and $HR_{constant}$ without leaving the scope of the invention.

Instead of measuring or estimating the $HR_{rest}$, it is also conceivable that the portable device comprises an input interface, that may for example be realized as a small key pad or touch pad that enables the user to manually type in his/her $HR_{rest}$. In this way, it is also conceivable that the user directly defines his/her personal fitness parameter a.

Instead of manually defining the fitness parameter a and measuring the motion frequency f, a much better method to determine the $HR_{constant}$ is to use previous measurement sessions of the same user.

According to an embodiment of the present invention, the portable device further comprises a storage unit which is adapted to store reference measures for heart rates belonging to known levels of intensity of the person's physical activity, wherein the processing unit is adapted to determine a level of intensity of the person's physical activity based on the generated motion signal, and to determine the heart rate constant ($HR_{constant}$) by comparing the determined level of intensity with the reference measures stored in said storage unit if the signal quality of the heart rate signal is below the threshold signal quality.

Said reference measures may be heart rate measurements that have been recorded from previous measurement sessions of the same user. If the user has performed a physical activity, such as e.g. running a day before using the same portable device, then the measured signals can be stored in the storage unit. By recording the heart rate signal together with the corresponding motion signal the calculated heart rates may be mapped/linked to the corresponding motion levels that are derived from the motion signal.

In this way, it is also possible to determine different heart rate constants that correspond to different levels of intensity of the person's physical activity using the previous measurements. For example, it is conceivable that a certain amount of intensity levels are mapped within the storage unit to corresponding heart rate constants. In this case, not necessarily all previous measurement data need to be stored in the storage unit.

The level of intensity of the person's physical activity may, for example, be determined based on the frequency, at least one peak value of the generated motion signal and/or based on the average level or amplitude of the generated motion signal over a time-interval. The level of intensity thus indicates a motion level, which is a measure for the physical load the person is subjected to during his/her physical activity.

The storage unit may, for example, be realized by a small microchip. The recording of the reference heart rates or reference heart rate constants can be performed automatically. Thereto, the processing unit switches to a recording mode, in which the processed heart rates and the corresponding motion intensity levels are concurrently stored in the storage unit during the measurement. Determining the heart rate constant based on stored reference measures, as this has been explained above, results in increased measurement efficiency. The user does no longer need to manually type in the parameters that are used to calculate the $HR_{constant}$ (parameters a, f).

A personalized $HR_{constant}$ may be determined in an efficient way by analyzing the previous recorded data. The deduced parameters are in this way personalized, so that their usage improves the future estimations of the heart rate in the transition periods, in which the processing unit switches to the second working mode.

According to a further embodiment of the present invention, the portable device further comprises a first input interface for receiving information about a type of physical activity of the person, wherein the processing unit is adapted to estimate the heart rate based on the motion signal and the type of physical activity if the signal quality of the heart rate signal is below said level of signal quality.

This first input interface may, for example, be realized as a small key pad that is integrated into the portable device. In this way, the user may manually select a type of physical activity he wants to perform. The user may, for example, be shown a selection list of different physical activities, such as e.g. running, cycling, rowing, weightlifting, etc.

If the type of physical activity is known in advance, this simplifies the determination of the motion frequency, since each type of physical activity in practice generates a different kind of pattern of the detected motion signal with a different expected average motion frequency. Having at least rough information about the expected motion frequency enables to safe processing time in the second mode of the processing unit in which the heart rate is estimated based on the motion signal.

The information about the type of physical activity may also allow to adapt the above-mentioned exponential approximation curve within the transition period. This meets the fact that the heart rate may have a different development over time for different kinds of physical activities, e.g. the heart rate may in-/decrease faster in a cycling activity compared to a weightlifting activity.

According to a further embodiment of the present invention, the portable device comprises a second input interface for receiving the person's personal data, in particular an age, a gender, a body weight, a body height and/or a resting heart rate, wherein the processing unit is adapted to estimate the heart rate based on the motion signal and the received personal data if the signal quality of the heart rate signal is below the above-mentioned threshold signal quality.

Instead of determining the personalized parameters from previous measurements as this has been explained above, it is also conceivable that the user manually enters his/her personal data that physiologically influence the heart rate and its development over time. Said second input interface may either be an extra key pad or realized by the same key pad that is used as first input interface.

The personal physiological user data may be either used to adapt the above-mentioned parameters to calculate the $HR_{constant}$ or they may be used to apply an additional physiological model, which model can then be used to adapt the above-mentioned heart rate development model during the transition period. Examples of such kind of physiological models are known from the prior art. Some exemplary models are, for example, known from the scientific paper "Reliability and Validity of the Combined Heart Rate and Movement Sensor Actiheart", European Journal of Clinical Nutrition (2005) 59, 561-570.

In summary, the presented portable device and the corresponding method allow to detect the heart rate of an athlete or a sportsman in many different situations, even in situations where large movements occur and state of the art optical heart rate sensors are not able to reliably detect the heart rate. As explained in the foregoing, the processing unit is adapted to switch between two modes. In the first mode, the heart is calculated based on the heart rate signal if the signal quality is above a predefined threshold. If on the other hand, the processing unit is not able to reliably calculate the heart rate based on the heart rate signal, the processing unit switches to a second mode in which the heart rate is estimated from motion, by using a model in which the data is compared with a set of values determined from previous measurements or introduced as input by the user. The presented method thereby makes use of one of the following features, or any combination thereof:

1. The history of the good measurements up to the point of failure,
2. an indication of the quality of the measurements made, which tells that the last measurement is a failure,
3. a profile of the user that can be either be pre-recorded or determined from the reliable measurements, and/or
4. a physiological model that makes use of parameters that are determined from previous measurements from the same user.

BRIEF DESCRIPTION OF THE DRAWINGS

These and other aspects of the invention will be apparent from and elucidated with reference to the embodiment(s) described hereinafter. Therein:

FIG. 5A shows a first example of a measured heart rate signal and FIG. 5B shows an example of a signal quality measurement corresponding to the measured heart rate signal shown in FIG. 5A, FIG. 6A shows a second example of a measured heart rate signal and FIG. 6B shows an example of a signal quality measurement corresponding to the measured heart rate signal shown in FIG. 6A, FIG. 7A shows a third example of a measured heart rate signal and FIG. 7B shows an example of a signal quality measurement corresponding to the measured heart rate signal shown in FIG. 7A, FIG. 8A shows the first example of a measured heart rate signal shown in FIG. 5A including a heart rate signal that has been estimated with the presented portable device according to the presented method and FIG. 8B shows the corresponding signal quality measurement, FIG. 9A shows the second example of a measured heart rate signal shown in FIG. 6A including a heart rate signal that has been estimated with the presented device according to the presented method and FIG. 9B shows the corresponding signal quality measurement, FIG. 10A shows the third example of a measured heart rate signal shown in FIG. 7A including a heart rate signal that has been estimated with the presented device according to the presented method and FIG. 10B shows the corresponding signal quality measurement, FIG. 11 schematically shows an appliance of a system according to the present invention.

DETAILED DESCRIPTION OF THE INVENTION

Figure 1:
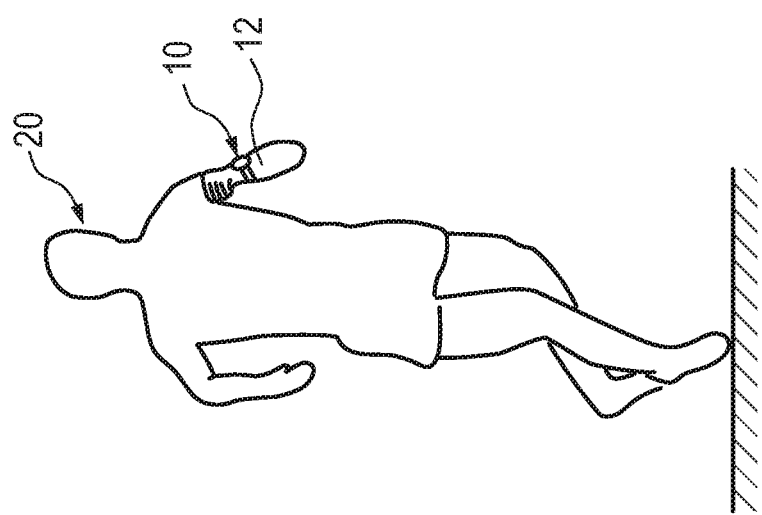
FIG. 1 shows a schematic appliance of a portable device according to the present invention.

FIG. 1 schematically shows an appliance of the portable device according to the present invention which is denoted by the reference numeral 10. A person 20 that is in this figure exemplarily shown as a runner wears the portable device 10 for measuring the pulse during his/her physical activity.

The portable device 10 is attached to a body part 12, which body part 12 is suitable for measuring the pulse of the person 20, i.e. a body part 12 on which the arterial blood pulse can easily be tracked. As shown in FIG. 1, the portable device is preferably attached to the wrist of the person 20. However, the portable device may also be attached to any other body part 12 of the person 20, e.g. the chest, a leg or around the neck.

Figure 2:
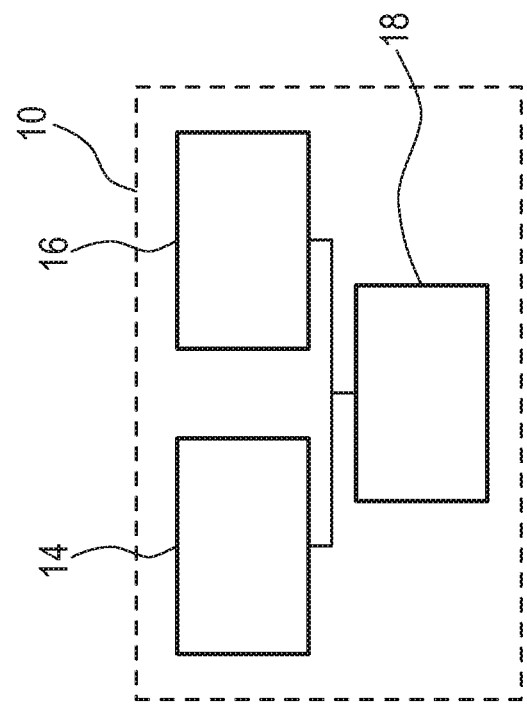
FIG. 2 shows a schematic block diagram illustrating the components of the portable device according to a first embodiment.

As this is shown in the schematic block diagram of FIG. 2 said portable device comprises a heart rate measurement unit 14, a motion measurement unit 16 and a processing unit 18. The heart rate measurement unit 14 and the motion measurement unit 16 are electronically coupled with the processing unit 18. The heart rate measurement unit 14 preferably comprises an optical sensor, in particular a photoplethysmography (PPG) sensor, which measures the blood pulse wave of the person 20 over time and generates a heart rate signal 22.

The PPG sensor includes a photodetector (not shown) that measures the absorbance of the blood at different wavelengths allowing a determination of the light absorbance changes that are due to the pulsing arterial blood. Such a kind of PPG sensor allows measuring the pulse of the person in a comfortable way.

The motion measurement unit 16 preferably comprises an inertial sensor for measuring an acceleration of said body part 12 in at least one spatial dimension, more preferably in all three spatial dimensions. This inertial sensor measures the motion of said body part 12 of the person 20 over time to generate an acceleration-over-time signal that records the occurring accelerations at the wrist of the person 20 to which the portable device 10 is preferably attached.

Figure 3:
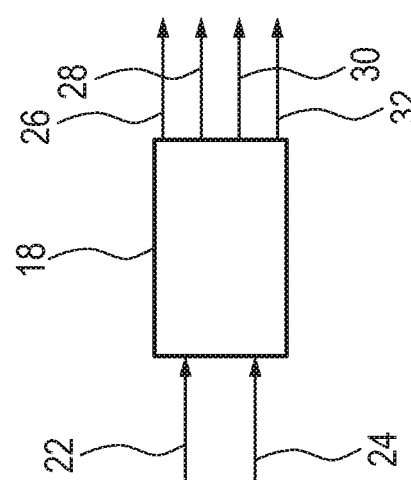
FIG. 3 shows a schematic block diagram illustrating in- and output signals of a processing unit of the portable device according to the first embodiment.

In this way, the processing unit 18 receives two signals that are measured in real time, the heart rate signal 22 and the motion signal 24. This is exemplarily shown in the illustrated block diagram of FIG. 3. The processing unit 18 analyzes the heart rate signal 22 and the motion signal 24. From this analysis the processing unit 18 calculates the heart rate 26 and the motion rate 28, wherein the motion rate 28 indicates the motion frequency with which the body part 12 is moved during the physical activity of the person 20.

The processing unit 18 further measures a signal quality 30 of the heart rate signal 22 and a signal quality 32 of the motion/acceleration signal 24. The signal quality 30, 32 indicates a measure for the data reliability of the measured signals 22, 24. It indicates the amount of noise that corrupts the measured signals 22, 24. A low noise corruption leads to a high signal quality 30, 32, whereas a high noise corruption leads to a correspondingly low signal quality 30, 32. The amount of noise corruption within the measured signals 22, 24 is measured in the processing unit 18 by performing a frequency analysis, as this has been explained in detail in the summary of the invention above.

Depending on the signal quality 30 of the heart rate signal 26 the processing unit 18 switches between two calculation modes. Thereto, a threshold is defined, said threshold indicating the level of noise within the heart rate signal 22, wherein the heart rate signal 22 that is measured by the heart rate measurement unit 14 becomes unreliable when exceeding said predefined level of noise, respectively when underrunning said threshold. Thus, the threshold indicates the minimum signal quality 30 of the heart rate signal 22 that is needed to reliably calculate the heart rate 26 based on the heart rate signal 22.

The processing unit 18 switches to the first calculation mode if the signal quality 30 of the heart rate signal 22 is above said predefined threshold. In this case, the processing unit 18 calculates the heart rate 26 based on the heart rate signal 22. This mode represents the "normal" mode in which the optical sensor of the heart rate measurement unit 14 delivers a reliable signal that includes only a few motion artifacts, which still enables to calculate the heart rate 26 based on the measured heart rate signal 22.

If, however, the portable device 10 is subjected to strong agitations (high accelerations) the signal quality 30 of the heart rate signal 22 may become so poor that a reliable calculation of the heart rate 26 is technically not possible anymore based on the heart rate signal 22. Such situations occur when the person 20 is moving the body part 12 in a fast and discontinuous way.

In such cases devices of the prior art using similar optical heart rate measurement sensors fail to measure the heart rate, which means that no reliable measurement is possible. However, this problem has been solved by the present invention.

In the cases described above, the processing unit 18 is adapted to switch to its second calculation mode, in which the heart rate 26 is estimated based on the motion signal 24. This estimation of the heart rate 26 starts as soon as the processing unit 18 recognizes that the signal quality 30 of the heart rate signal 22 falls below the predefined quality threshold. The processing unit 18 then estimates the heart rate 26 using a physiological model that makes use of the signal data taken from the motion signal 24. This estimation is, according to an embodiment, done as follows. In a first step, the processing unit 18 estimates an $HR_{constant}$. This $HR_{constant}$ indicates a pulse level of the person to which the person's pulse would increase or decrease if the amount and intensity of motion would be kept constant for a long time.

Figures 11, 12:
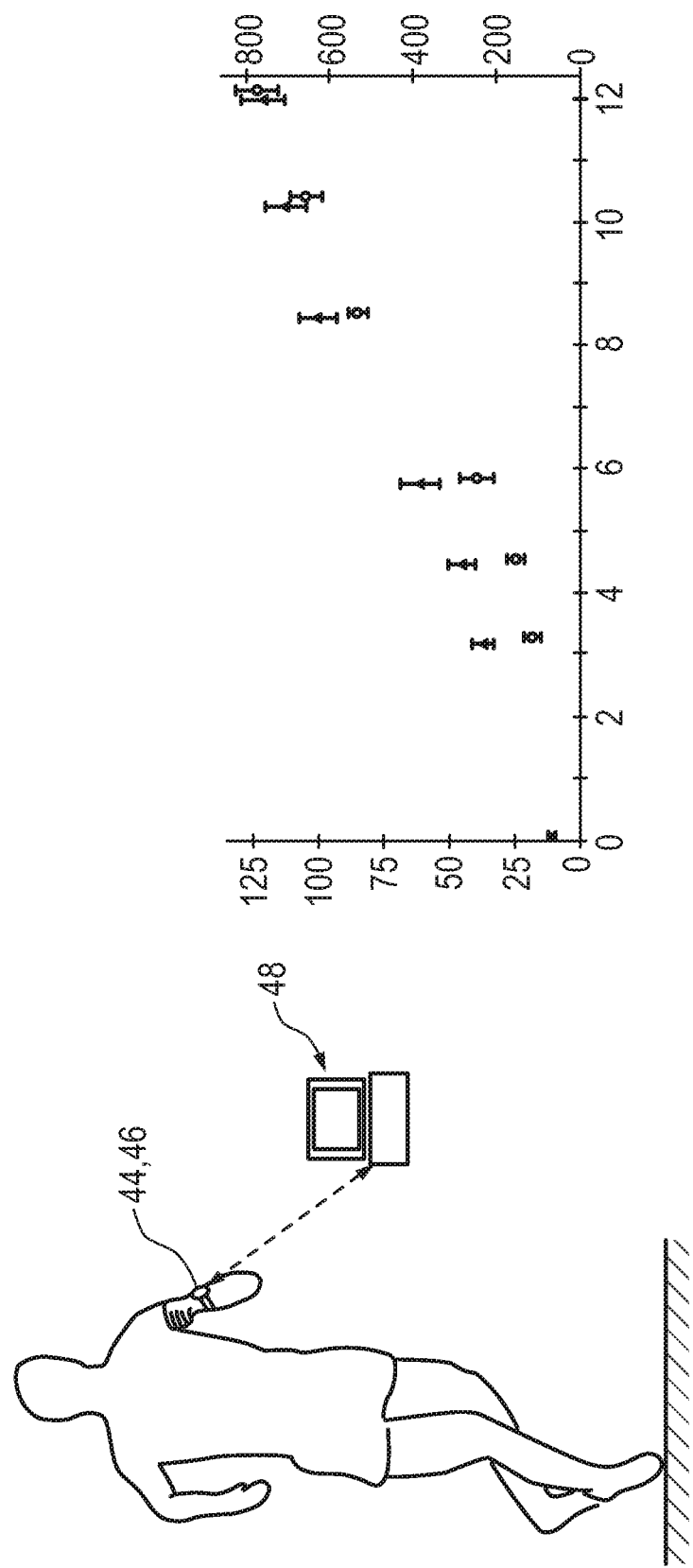
FIG. 12 shows an exemplary diagram illustrating a relation between the heart rate and the power/intensity of a physical exercise.

As it can be seen from the exemplary diagram shown in FIG. 12, there is a linear relation between the heart rate 26 and the power of the effort of a physical exercise. In this diagram, the X-axis shows the speed of a runner measured in kph, the left Y-axis shows the heart rate above sleep in bpm, and the right Y-axis shows the power of the exercise (PAI) expressed in J/min/kg. This plot was made from an experiment with about 30 persons, whose pulse was measured during running with different running speeds and intensity levels. It shows that there is a linear relation between the heart rate and the power/intensity with which the running activity is performed. This plot has been published in 2005 in the European Journal of Clinical Nutrition (2005) 59, 561-570, "Reliability and Validity of the Combined Heart Rate and Movement Sensor Actiheart".

Experiments performed by the applicant have shown that the $HR_{constant}$ more or less equals a value that is about two times the frequency of the motion. Thus, the estimation of the $HR_{constant}$ requires an estimation of the present motion, respectively an estimation of the frequency of the motion of the measured body part 12.

This frequency is derived from a spectral analysis of the motion signal 24. Once the $HR_{constant}$ is determined, the processing unit 18 produces an approximation curve that represents the estimated heart rate development over time for the time period in which the processing unit 18 is switched to the second mode (transition period), in which the optical heart rate sensor 14 does not deliver a reliable signal 22. This approximation curve takes the last reliably measured heart rate 26 as its start value and the estimated $HR_{constant}$ as its terminal value. In between these two values an exponential approximation curve is applied. It has been shown that an exponential development reflects the natural behavior of the human heart in a good and precise manner.

Since the so-called transition period, in which the optical heart rate sensor 14 fails to measure, is in practice only a very short time period of several seconds, this assumption has shown to result in a good approximation. Experiments performed by the applicant have further shown that the described exponential development of the pulse adaption also depends on the fitness of the person 20.

A fitness factor a, which denotes the fitness level of the person 20, is thus preferably integrated in addition. Experiments have shown that an exponential approximation curve, where the time constant is given by the fitness factor a results in a rather good estimation of the heart rate development during the transition period. The fitness factor a in this case denotes a constant related to the person's fitness in such a way, that a decreases with increasing fitness of the person 20.

Figure 4:
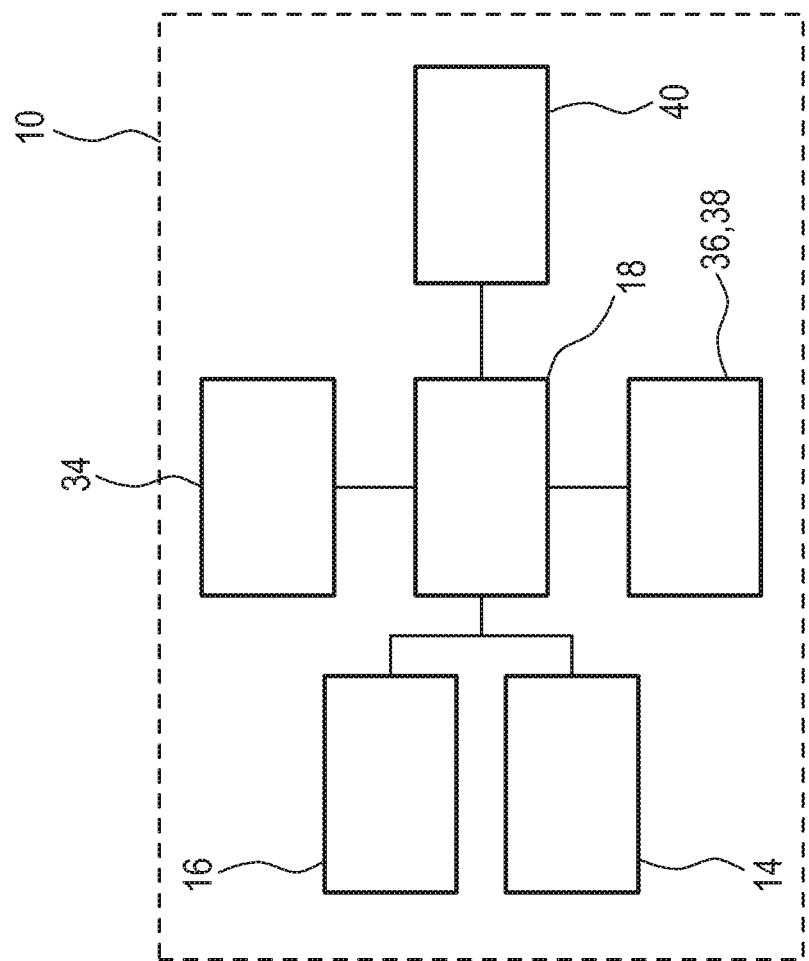
FIG. 4 shows a schematic block diagram illustrating the components of the portable device according to a second embodiment.

The estimation of the heart rate development during the transition period may be further improved by taking into account previous measurement sessions of the same user 20. The $HR_{constant}$ may thus be determined based on stored previous measurement data. To implement this, the portable device 10 comprises, according to a second embodiment that is shown in FIG. 4, an additional storage unit 34 which is adapted to store reference measures for heart rates 26 belonging to reference levels of intensity of the person's physical activity. According to this embodiment, the processing unit 18 is adapted to determine a level of intensity of the person's physical activity based on the generated motion signal 24, and to determine the heart rate constant ($HR_{constant}$) by comparing the determined level of intensity with the reference measures stored in said storage unit 34.

Said reference measures may be heart rate measurements that have been recorded from previous measurement sessions of the same user 20. If the user 20 has performed a physical activity, such as e.g. running a day before using the same portable device 10, then the measured signals can be stored in the storage unit 34. By recording the heart rate signal 22 together with the corresponding motion signal 24, the calculated heart rate 26 may be linked to the corresponding motion levels that are derived from the motion signal 24. In this way, the processing unit 18 is enabled to determine different heart rate constants that correspond to different levels of intensity of the person's physical activity using the previous measurements.

The level of intensity of the person's physical activity may, for example, be determined based on the frequency, at least one peak value of the generated motion signal 24 and/or based on the average level or amplitude of the generated motion signal 24 over a time interval. The level of intensity thus indicates a motion level, which is a measure for the physical load of the person.

In practice, the storage unit 34 is realized by a small microchip. By including an additional storage unit 34 the estimation of the $HR_{constant}$ and thus also the estimation of the heart rate development during the transition period becomes more efficient. The processing unit 18 analyses the previous recorded data and uses the parameters deduced from this data for the estimation of the heart rate development during the transition period.

As exemplarily shown in the block diagram of FIG. 4, the portable device 10 may further include a first input interface 36, e.g. a small key pad or touch pad that allows the user 20 to manually select a type of physical activity he wants to perform. The user 20 may, for example, select a physical activity, such as running, cycling, rowing or weightlifting, from a predefined list. If the processing unit 18 additionally receives information about the type of physical activity, this simplifies the determination of the motion frequency. This again relies on the fact, that each type of physical activity in practice generates a different kind of pattern of the detection motion signal 24.

As further shown in the block diagram of FIG. 4, the portable device may additionally comprise a second input interface 38. This second input interface 38 may also be a key pad or touch pad that the user 20 uses to manually enter his/her personal data that physiologically influence the heart rate and its development over time. Possibly important personal data may be e.g. the age, the gender, the body weight, the body height and/or the resting heart rate.

Thus, the user 20 may directly enter his personal data that can be used to improve the estimation of the heart rate 26 in the second mode of the processing unit 18, when the optical heart rate sensor 14 fails to deliver a reliable heart rate signal 22. The entered personal data may also be used to apply an additional physiological model, which model can be used to adapt the estimated heart rate development during the transition period. Exemplary physiological models are known from the above-mentioned scientific paper.

It is to be noted that this second input interface 38 is not necessarily needed, since at least a few of the personal parameters, such as the $HR_{rest}$ and the personal fitness parameter a, may also be derived from the motion signal 24 in the way mentioned above. Further, it is to be noted that the first input interface 36 and the second input interface 38 may be realized by the same key pad (as this is schematically illustrated in FIG. 4).

According to the illustrated second embodiment, the portable device 10 furthermore comprises a display 40. The display 40 may, for example, be a small LED array that is integrated into the portable device 10 and used to visualize/display the calculated heart rate 26 to the user 20 in real time.

FIGS. 5A to 7A show three exemplary measurements that have been recorded with an optical heart rate sensor during a running activity of the user 20. The top diagrams (FIGS. 5A, 6A and 7A) show the heart rate signal 22, 22', 22", measured in beats per minute (Y-axis), over the time, measured in seconds (X-axis). The bottom diagrams (FIGS. 5B, 6B and 7B) show the corresponding recorded heart rate quality signal 30, 30', 30" and the motion rate quality signal 32, 32', 32" over the corresponding time periods.

The measurements shown in FIGS. 5A, 6A and 7A show the uncorrected heart rate signal 22, 22', 22", meaning that these heart rate signals 22, 22', 22" have only been measured with the optical heart rate measurement unit 14 and have not been corrected by the received motion data.

In FIG. 5A, it can be seen that this heart rate measurement fails in the time period between 500 and 700 sec (time period highlighted with circles). In this time period, the heart rate quality signal 30 is very low and tends to almost zero. The motion rate quality signal 32 instead shows rather high values, which is an indicator that there is a large movement of the portable device 10. This results in an unreliable development of the heart rate signal 22 within this time period.

In this time period the measured heart rate signal 22 has a very discontinuous development including strong variations, which of course does not match the "real" heart rate behavior. This relies on the above-mentioned effect that large motion artifacts are introduced into the heart rate signal 22 if high accelerations occur.

Similar examples are shown in FIGS. 6A, 6B, 7A and 7B. Herein, the failure of the heart rate measurement unit 14 occurs in the time period of 400 to 700 sec (FIG. 6A) or of 100 to 700 sec (FIG. 7A). This is identified by the corresponding heart rate quality signals 30', 30" that become very low in these time periods and indicate that the measured heart rate data cannot be relied upon.

FIGS. 8A, to 10 show the same graphs, wherein the estimated heart rate signals 23, 23', 23" that have been calculated/estimated using the presented portable device 10 are plotted therein as well. FIG. 8 refers to the same failure instance as FIG. 5, FIG. 9 to the one of FIG. 6, and FIG. 10 to the one of FIG. 7. The graphs furthermore include a plot of the "real" heart rate signals 42 that have been measured with an ECG device in order to receive the real heart rate development as a reference.

It can be seen from FIGS. 8 to 10 that the heart rate signals 23, 23', 23" estimated with the portable device 10 are very close to the reference signals 42, 42', 42". It has to be noted that the estimated heart rate signals 23, 23', 23" have been estimated based on the motion signal 24 in the way explained above. In the time periods, in which the heart rate measurement unit 14 delivers reliable measurement results (e.g. in the time periods 0 to 400 and 700 to 1850 in the examples shown in FIGS. 6 and 9), the heart rate signals 23, 23', 23" are the heart rate signals which are directly measured with the heart rate measurement unit 14. In the time periods, in which the measurement of the heart rate measurement unit 14 fails (e.g. in the time period 400 to 700 sec in FIGS. 6 and 9), the heart rate signal 23, 23', 23" is estimated based on the motion signal 24 using one of the above-mentioned estimation methods. This results in a rather realistic heart rate calculation/estimation at all times of the measurement.

The presented portable device and the corresponding method allow to detect the heart rate of an athlete or a sportsman in many different situations, even in situations where large movements occur and a state of the art optical heart rate sensor would not be able to reliably detect the heart rate. As explained in the foregoing, the processing unit is adapted to switch between two modes. In the first mode, the heart rate is calculated based on the heart rate signal if the signal quality is above a predefined threshold. If on the other hand, the processing unit is not able to reliably calculate the heart rate based on the heart rate signal, the processing unit switches to a second mode in which the heart rate is estimated from motion, by using a model in which the data is compared with a set of values determined from previous measurements or introduced as input by the user. The presented method thereby makes use of one of the following features, or any combination thereof:

1. The history of the good measurements up to the point of failure,
2. an indication of the quality of the measurements made, which tells that the last measurement is a failure,
3. a profile of the user that can be either be pre-recorded or determined from the reliable measurements, and/or
4. a physiological model that makes use of parameters that are determined from previous measurements from the same user.

As it can be seen from FIG. 11, the presented method does not necessarily need to be implemented in a portable device 10. Similarly, a system 100 may be provided that comprises a portable heart rate measurement device 44 and a portable motion measurement device 46 that may be included into the same casing. The difference between the shown system 100 and the portable device 10 is that no portable processing unit 18 is integrated into the portable device. Instead, the signals measured by the portable heart rate measurement device 44 and the portable motion measurement device 46 may be transferred to an external processing device 48 which performs the above-mentioned calculations/estimations externally. By using a wireless connection between the portable devices 44, 46 and the processing device 48 this data transfer may also be realized in real time. However, it is also possible that the data recorded by the portable devices 44, 46 are stored in a storage unit and transferred afterwards to the processing device 48 (after the measurement).

In order to establish a real time connection, the portable devices 44, 46 preferably comprise a communication interface (for simplicity reasons not shown) such as e.g. a radio transmitter, whereas the processing device also includes a similar communication interface such as e.g. a radio receiver. For the rest, it shall be understood that the system 100 has similar and/or identical preferred embodiments as the claimed portable device 10.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A portable device for determining a heart rate of a person, said portable device comprising:
  a heart rate sensor for measuring the heart rate of the person over time to generate a heart rate signal;
  an inertial sensor for measuring the motion of a body part of the person over time to generate a motion signal; and
  a processing unit which is adapted to:
    measure via signal analysis of the heart rate signal a signal quality of the heart rate signal;
    calculate the heart rate based on the heart rate signal if said measured signal quality is above a predefined threshold; and
    estimate the heart rate based on the motion signal if said measured signal quality is below said threshold by estimating a heart rate constant ($HR_{constant}$) and defining an exponential development of the heart rate over time, wherein the exponential development includes an exponential curve indicating the heart rate over time, wherein the exponential curve is based on the person's fitness.

2. The portable device of claim 1, wherein the exponential development of the heart rate starts at a last reliably measured heart rate and finishes at the estimated $HR_{constant}$, the estimated $HR_{constant}$ depending on a frequency of the motion signal, and the last reliably measured heart rate being the last measured heart rate with the heart rate sensor at a time before falling below said threshold.

3. A portable device for determining a heart rate of a person, said portable device comprising:
  a heart rate sensor for measuring the heart rate of the person over time to generate a heart rate signal;
  an inertial sensor for measuring the motion of a body part of the person over time to generate a motion signal; and
  a processing unit which is adapted to:
    measure via signal analysis of the heart rate signal a measured signal quality of the heart rate signal;
    calculate the heart rate based on the heart rate signal if said measured signal quality is above a predefined threshold; and
    estimate the heart rate based on the motion signal if said measured signal quality is below said threshold, wherein the processing unit is adapted to estimate the heart rate by estimating a heart rate constant ($HR_{constant}$) and defining an exponential development of the heart rate over time, wherein the exponential development includes an exponential curve indicating the heart rate over time and wherein the exponential curve is based on the person's fitness.

4. The portable device of claim 3, wherein the exponential development of the heart rate starts at a last reliably measured heart rate and finishes at the estimated $HR_{constant}$, the estimated $HR_{constant}$ depending on a frequency of the motion signal, and the last reliably measured heart rate being the last measured heart rate with the heart rate sensor at a time before falling below said threshold.

5. The portable device of claim 3, wherein the heart rate sensor comprises an optical sensor, the optical sensor comprising a photoplethysmography (PPG) sensor for measuring a blood pulse wave of the person over time to generate the heart rate signal.

6. The portable device of claim 3, further comprising a display for displaying the calculated heart rate.

7. The portable device of claim 3, further comprising a storage unit which is adapted to store reference measures for heart rates belonging to known levels of intensity of the person's physical activity, wherein the processing unit is adapted to determine a level of intensity of the person's physical activity based on the generated motion signal and to estimate the heart rate constant ($HR_{constant}$) by comparing the determined level of intensity with the reference measures stored in said storage unit if the measured signal quality of the heart rate signal is below said threshold.

8. The portable device of claim 3, further comprising an input interface for receiving information about a type of physical activity of the person, wherein the processing unit is adapted to estimate the heart rate based on the motion signal and the type of physical activity if the measured signal quality of the heart rate signal is below said threshold.

9. The portable device of claim 3, further comprising an input interface for receiving the person's personal data, the person's personal data comprising one or any combination of an age, a gender, a body weight, a body height or a resting heart rate, wherein the processing unit is adapted to estimate the heart rate based on the motion signal and the received personal data if the measured signal quality of the heart rate signal is below said threshold.

10. The portable device of claim 3, further comprising a frequency filter to filter out the frequency components within the heart rate signal which are due to motion of the device, and wherein the processing unit is adapted to determine the signal quality of the filtered heart rate signal.

11. A method for determining a heart rate of a person, the method comprising:
   measuring the heart rate of the person over time to generate a heart rate signal;
   measuring the motion of a body part of the person over time to generate a motion signal;
   measuring via signal analysis of the heart rate signal a signal quality of the heart rate signal;
   calculating the heart rate based on the heart rate signal if said measured signal quality is above a predefined threshold; and
   estimating the heart rate based on the motion signal if said measured signal quality is below said threshold, wherein the estimating includes estimating a heart rate constant ($HR_{constant}$) and defining an exponential development of the heart rate over time, wherein the exponential development includes an exponential curve indicating the heart rate over time, wherein the exponential curve is based on the person's fitness.

12. The method of claim 11, wherein the exponential development of the heart rate starts at a last reliably measured heart rate and finishes at the estimated $HR_{constant}$, the estimated $HR_{constant}$ depending on a frequency of the motion signal, and the last reliably measured heart rate being the last measured heart rate at a time before falling below said threshold.

13. A non-transitory, computer readable medium comprising program code that, when executed by a processing device, causes the processing device to:
   receive a heart rate signal;
   receive a motion signal;
   measure via signal analysis of the heart rate signal a signal quality of the heart rate signal;
   calculate a heart rate based on the heart rate signal if said measured signal quality is above a predefined threshold; and
   estimate the heart rate based on the motion signal if said measured signal quality is below said threshold by estimating a heart rate constant ($HR_{constant}$) and defining an exponential development of the heart rate over time, wherein the exponential development includes an exponential curve indicating the heart rate over time, wherein the exponential curve has a time constant a, a being a constant related to the person's fitness which decreases with increasing fitness.

14. The non-transitory, computer readable medium of claim 13, wherein
   the exponential development of the heart rate starts at a last reliably measured heart rate and finishes at the estimated $HR_{constant}$, the estimated $HR_{constant}$ depending on a frequency of the motion signal, and the last reliably measured heart rate being the last measured heart rate with the heart rate sensor at a time before falling below said threshold.

* * * * *